(12) United States Patent
Fisker

(10) Patent No.: US 10,357,344 B2
(45) Date of Patent: Jul. 23, 2019

(54) METHOD FOR MANUFACTURING A DENTURE

(71) Applicant: 3SHAPE A/S, Copenhagen K (DK)

(72) Inventor: Rune Fisker, Virum (DK)

(73) Assignee: 3Shape A/S, Copenhagen K (DK)

(*) Notice: Subject to any disclaimer, the term of this patent is extended or adjusted under 35 U.S.C. 154(b) by 145 days.

(21) Appl. No.: 15/510,796

(22) PCT Filed: Sep. 15, 2015

(86) PCT No.: PCT/EP2015/071047
§ 371 (c)(1),
(2) Date: Mar. 13, 2017

(87) PCT Pub. No.: WO2016/041937
PCT Pub. Date: Mar. 24, 2016

(65) Prior Publication Data
US 2017/0273766 A1 Sep. 28, 2017

(30) Foreign Application Priority Data

Sep. 15, 2014 (DK) .................................. 2014 70568

(51) Int. Cl.
*A61C 13/00* (2006.01)
*A61C 13/01* (2006.01)
(Continued)

(52) U.S. Cl.
CPC .......... *A61C 13/01* (2013.01); *A61C 13/0019* (2013.01); *A61C 13/1016* (2013.01);
(Continued)

(58) Field of Classification Search
CPC ......... Y10T 29/49567; Y10T 29/49568; A61C 13/01; A61C 13/0006; A61C 13/1016
See application file for complete search history.

(56) References Cited

U.S. PATENT DOCUMENTS

2015/0216638 A1  8/2015  Baaske et al.

FOREIGN PATENT DOCUMENTS

EP   2 742 907 A1   6/2014
FR   2 992 163 A3   12/2013
(Continued)

OTHER PUBLICATIONS

English Translation Watzke EP 2742907 (Year: 2014).*
(Continued)

*Primary Examiner* — Jason L Vaughan
*Assistant Examiner* — Amanda Kreiling
(74) *Attorney, Agent, or Firm* — Buchanan Ingersoll & Rooney PC

(57) ABSTRACT

There is disclosed a method for manufacturing a denture comprising an artificial gingiva surface, a seating surface facing at least a part of the gingiva surface when placed in the mouth of a patient, at least one tooth receiving hole provided in the artificial gingiva surface and extending through to the seating surface and an artificial tooth arranged in the tooth receiving hole, The method comprises printing an intermediate denture base comprising the artificial gingiva surface, the at least one tooth receiving hole for receiving the artificial tooth, arranging the artificial tooth in the at least one tooth receiving hole, fixing the intermediate denture base in a milling machine, and milling the denture comprising providing the seating surface by removing at least a part of the tooth extending through the tooth receiving hole. This provides an improved manufacturing process of denture.

5 Claims, 1 Drawing Sheet

(51) Int. Cl.
  *B33Y 10/00*    (2015.01)
  *B33Y 80/00*    (2015.01)
  *A61C 13/36*    (2006.01)
  *B29C 64/00*    (2017.01)
  *B29L 31/00*    (2006.01)

(52) U.S. Cl.
  CPC .............. *B29C 64/00* (2017.08); *B33Y 10/00* (2014.12); *B33Y 80/00* (2014.12); *A61C 13/0006* (2013.01); *A61C 13/0013* (2013.01); *B29L 2031/7536* (2013.01)

(56) References Cited

FOREIGN PATENT DOCUMENTS

| JP | 1-155842 A | 6/1989 |
|----|------------|--------|
| WO | WO 2013/124452 A1 | 8/2013 |

OTHER PUBLICATIONS

English Translation Desforges FR 2992163 (Year: 2013).*
International Search Report (PCT/ISA/210) dated Dec. 10, 2015, by the European Patent Office as the International Searching Authority for International Application No. PCT/EP2015/071047.

* cited by examiner

METHOD FOR MANUFACTURING A DENTURE

FIELD OF THE INVENTION

This invention generally relates to manufacturing a denture. In particular, it relates to a method that comprises printing of the denture base and subsequent milling thereof in order to take advantage of both techniques.

BACKGROUND OF THE INVENTION

Denture manufacturing is very complex, and although the introduction of many digital processes have facilitated the manufacturing process, further improvement is still possible.

In particular, as will described herein a further improved manufacturing method may be obtained by using both 3D printing (additive manufacturing) and milling (subtractive manufacturing) in the manufacturing process.

SUMMARY

In one aspect the invention relates to a method for manufacturing a denture comprising an artificial gingiva surface, a seating surface facing at least a part of the gingiva surface when placed in the mouth of a patient, at least one tooth receiving hole provided in the artificial gingiva surface and extending through to the seating surface and an artificial tooth arranged in the tooth receiving hole, comprising
  printing an intermediate denture base comprising the artificial gingiva surface, the at least one tooth receiving hole for receiving the artificial tooth,
  arranging the artificial tooth in the at least one tooth receiving hole,
  fixing the intermediate denture base in a milling machine, and
  milling the denture comprising providing the seating surface by removing at least a part of the tooth extending through the tooth receiving hole.

When manufacturing large and complex objects 3D printing is becoming the preferred manufacturing process compared to milling. As 3D printing is an additive manufacturing process only the material needed is used in the process, whereas with milling which is a subtractive manufacturing process a lot of material is wasted as large volumes of unwanted material is removed with large objects.

Moreover, complex shapes such as a denture base as described herein often requires advanced milling machines such as five axis machines.

Accordingly, introduction of a printing step wherein the more complex and larger parts are manufactured, provides an improved manufacturing process where a lot of material can be saved when printing the denture base instead of milling. However, by maintaining a milling step the library teeth which comes as standard components can be milled to fit the denture. Since the library teeth are smaller components compared to the denture there is not a lot of material waste in milling these.

The artificial gingiva surface of the denture base is the surface that represents the gingiva when the denture is placed in the mouth of the patient. In other words, this is the visible surface of the denture base when in place and therefore has to have a realistic and esthetical appearance that closely resembles that of real gingiva.

The seating surface is typically opposite the artificial gingiva surface, however, in transition areas they will transition into each other. When the denture is in place in the patient's mouth the seating surface will face the gingiva of the patient and typically be seated against the gingiva applying light pressure. Accordingly, the seating surface is the finished gingiva facing surface of the denture after milling, ie. the surface comprises part of the denture base and part of the milled artificial tooth. In some cases the seating surface provides a friction grip with the gingiva which allows the denture to be retained in the mouth of the patient, however, in other cases the denture is retained by implant or snap/ball coupling wherein the seating surface provides little effect in retaining the denture.

In one embodiment the method further comprises,
  printing at least one milling fixture connected to the intermediate denture base, and
  fixing the intermediate denture base in the milling machine by fixing the milling fixture to a denture fixture provided in the milling machine.

The milling fixture may for example be adapted to attach to a milling holder. The milling holder provides a standard interface with common type blank holders, such as blank holder for holding 98 mm blanks. Such blank holders are well known and commonly used in milling machines.

In one embodiment the step of milling the denture comprises removing excess material provided during printing in order to provide the seating surface. This allows for a final treatment of the denture base after the artificial teeth have been fixed therein.

In another embodiment a bridge of excess material is provided during printing in order to close off one end of the at least one tooth receiving hole, thereby providing a tooth receiving cavity, and removing the bridge of excess material during milling in order to provide the seating surface.

The tooth receiving cavity formed by the through going hole and the bridge provides a stable pocket wherein the artificial tooth can be placed before the milling step. In particular it provides a larger gluing area wherein the artificial tooth can settle and cure before the bridge of excess material and the part of the tooth extending out of the through going hole is milled away to provide the seating surface.

In one embodiment the tooth receiving cavity matches the shape of the nonvisible part of the artificial tooth, which represents the neck and root part of the artificial tooth.

In some situations, depending on the precision of the manufacturing devices, it can be important to consider the tolerances of the manufacturing device. In such case there should be designed some slack into the milling fixtures in order to allow placement of the intermediate denture base in the milling machine. When such slack is incorporated into the design it is important to be able to uniquely identify the position of the printed intermediate denture in the milling machine. This can be achieved by providing identifiers on the intermediate denture base that can be recognized by e.g. cameras mounted on the milling machine.

If the printing manufacturing device has very low tolerance it may even be necessary to rescan the intermediate denture base. The digital model of the intermediate denture base can then be used to align the intermediate denture base exactly in the milling machine.

BRIEF DESCRIPTION OF THE DRAWINGS

The above and/or additional objects, features and advantages of the present invention, will be further elucidated by the following illustrative and non-limiting detailed description of embodiments of the present invention, with reference to the appended drawings, wherein.

DETAILED DESCRIPTION

In the following description, reference is made to the accompanying figures, which show by way of illustration how the invention may be practiced.

An intermediate denture base 1 is printed by using 3D printing techniques as known in the art. The intermediate denture base comprises an artificial gingiva surface 2. A tooth receiving cavity 3 is formed in intermediate denture base.

Figure 1:
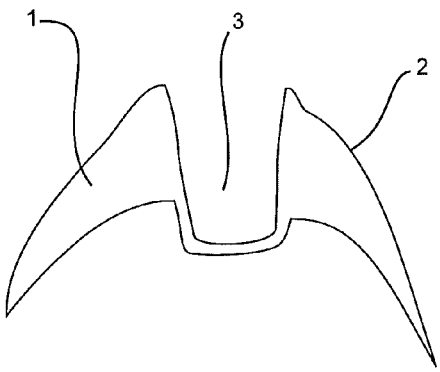
FIGS. 1-5 illustrates the steps of an embodiment of the invention.
Figure 2:
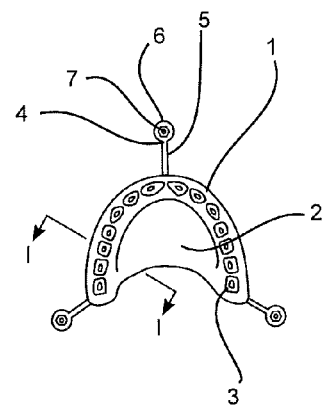
Figure 3:
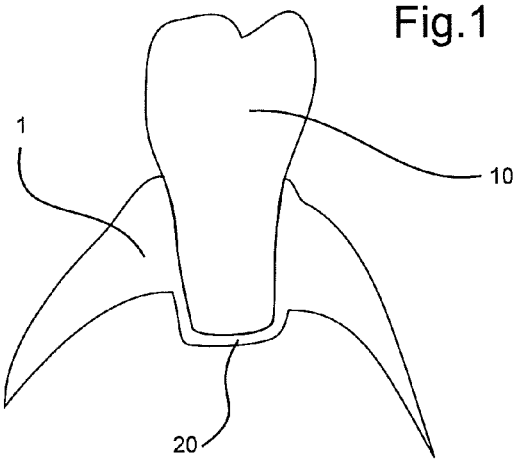

A sectional view of the intermediate denture base is shown in FIG. 1 and a top view of the intermediate denture base is shown in FIG. 2. The sectional view in FIG. 1 is seen along section I-I in FIG. 2. Three milling fixtures 4 are printed along with the denture base. The milling fixtures extend radially from the intermediate denture base and are formed by milling fixture arms 5 and a milling fixture attachment cylinder 6. The attachment cylinder is provided with a through going fixture bore 7.

After printing, artificial teeth 10 are placed in corresponding teeth receiving cavities 3. The artificial teeth are typically standard library teeth which can be bought from different suppliers. These library teeth are usually injection molded and provided in a number of variations of shapes and color so that a set suitable for individual patients can be obtained.

In order to ensure the position of the artificial teeth they are glued in place. The glue is preferably a material similar or identical to the denture base, typically an acrylic.

In order to ensure that the artificial teeth are fixed correctly a holder or other temporary fixation means can be used in order to ensure that the teeth are fixated in their correct position providing the proper occlusion when in use.

After the artificial teeth have been placed in the intermediate denture base the denture base is placed in a milling holder 15. The milling holder has a cylindrical shape that allows it to fit into common and well known blank holders (not shown) that fit in typical milling machines. The blank holder can for example be a holder used to hold standard 98 mm milling blanks, which are commonly used in the dental industry to mill restorations from 98 mm blanks.

Figure 4:
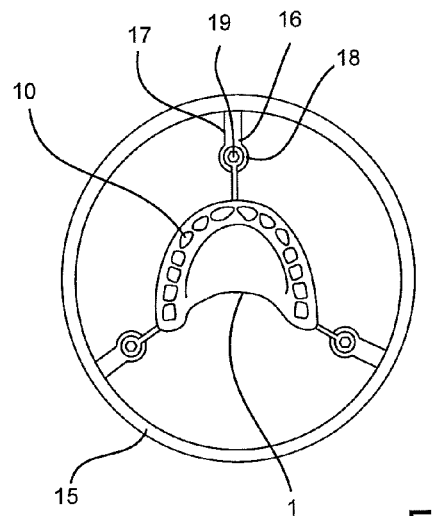
Figure 5:
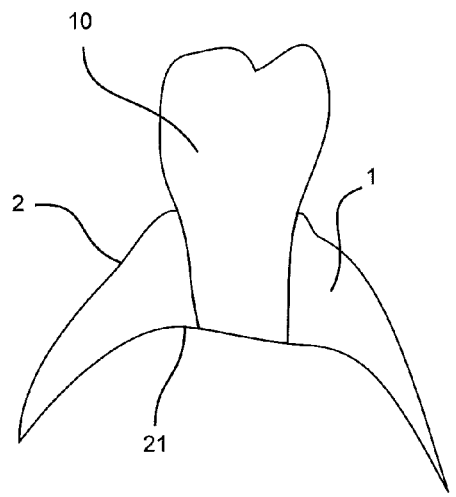

The milling holder 15 has three denture fixtures 16 that extend radially inwards along denture fixture arms 17 and terminates in denture fixture cups 18 wherein the milling fixture attachment cylinders 6 are received as shown in FIG. 4. In order to fix the intermediate denture base to the milling holder the cups and cylinders are secured with unbrako screws 19.

With the intermediate denture base along with the artificial teeth securely fixed in the milling holder the milling holder is placed in a milling machine and the seating surface 21 is provided by milling away excess material. This is also referred to as basal reduction. The seating surface is the surface of the denture which faces the patients gingiva.

In the current case some of the seating surface was already provided during printing. However, in order to better retain the artificial tooth a bridge 20 of material is provided in one end of the cavity 3. In order to finish the denture this bridge of material and the part of the artificial tooth contained therein is removed by the milling machine. As a result a smooth finish of the seating surface 21 is provided.

Although some embodiments have been described and shown in detail, the invention is not restricted to them, but may also be embodied in other ways within the scope of the subject matter defined in the following claims. In particular, it is to be understood that other embodiments may be utilised and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

The invention claimed is:

1. A method for manufacturing a denture comprising an artificial gingiva surface, a seating surface facing at least a part of a gingiva surface of a patient when placed in the mouth of the patient, at least one tooth receiving hole provided in the artificial gingiva surface and extending through to the seating surface and an artificial tooth arranged in the tooth receiving hole, comprising printing an intermediate denture base comprising the artificial gingiva surface and the at least one tooth receiving hole for receiving the artificial tooth, arranging the artificial tooth in the at least one tooth receiving hole, fixing the intermediate denture base in a milling machine and milling the denture comprising providing the seating surface by removing at least a part of the tooth extending through the tooth receiving hole.

2. A method according to claim 1, wherein the method further comprises, printing at least one milling fixture connected to the intermediate denture base, and fixing the intermediate denture base in the milling, machine by fixing the milling fixture to a denture fixture provided in the milling machine.

3. A method according to claim 1, wherein the step of milling the denture comprises removing excess material provided during printing in order to provide the seating surface.

4. A method according to claim 1, wherein a bridge of excess material is provided during printing in order to close off one end of the at least one tooth receiving hole, thereby providing a tooth receiving cavity, and removing the bridge of excess material during milling in order to provide the seating surface.

5. A method according to claim 4, wherein the tooth receiving cavity matches the shape of the neck and root part of the artificial tooth placed therein.

\* \* \* \* \*